(12) United States Patent
Sasaki et al.

(10) Patent No.: US 12,163,943 B2
(45) Date of Patent: Dec. 10, 2024

(54) PLANT BIOSENSOR

(71) Applicant: OMRON Corporation, Kyoto (JP)

(72) Inventors: Sho Sasaki, Kyoto (JP); Ryoji Shimizu, Kyoto (JP); Muneharu Miyakoshi, Kyoto (JP); Takaaki Miyaji, Kyoto (JP)

(73) Assignee: OMRON CORPORATION, Kyoto (JP)

( * ) Notice: Subject to any disclaimer, the term of this patent is extended or adjusted under 35 U.S.C. 154(b) by 292 days.

(21) Appl. No.: 17/773,634

(22) PCT Filed: Oct. 29, 2020

(86) PCT No.: PCT/JP2020/040639
§ 371 (c)(1),
(2) Date: May 2, 2022

(87) PCT Pub. No.: WO2021/085533
PCT Pub. Date: May 6, 2021

(65) Prior Publication Data
US 2022/0377991 A1  Dec. 1, 2022

(30) Foreign Application Priority Data

Nov. 1, 2019  (JP) .................. 2019-200153

(51) Int. Cl.
*G01F 1/684* (2006.01)
*G01N 33/00* (2006.01)

(52) U.S. Cl.
CPC ......... *G01N 33/0098* (2013.01); *G01F 1/684* (2013.01)

(58) Field of Classification Search
CPC .......... G01F 1/68–699; G01N 33/0098; G01D 11/24; G01D 11/245
See application file for complete search history.

(56) References Cited

U.S. PATENT DOCUMENTS

| 4,817,427 | A | * | 4/1989 | Kitano | .................. G01F 1/6847 47/1.01 R |
| 5,269,183 | A | | 12/1993 | Van Bavel et al. | |
| 5,367,905 | A | * | 11/1994 | Senock | ..................... G01F 1/68 73/204.22 |
| 6,397,162 | B1 | * | 5/2002 | Ton | ......................... A01G 7/00 702/136 |

(Continued)

FOREIGN PATENT DOCUMENTS

| CN | 101038192 A | 9/2007 |
| CN | 106508216 A | 3/2017 |

(Continued)

OTHER PUBLICATIONS

CNIPA Notification of the First Office Action for corresponding CN Application No. 2020800761773; Issue Date, Jun. 1, 2023.

(Continued)

*Primary Examiner* — Justin N Olamit
(74) *Attorney, Agent, or Firm* — CANTOR COLBURN LLP

(57) ABSTRACT

A plant biosensor includes a solar radiation sensor that measures a solar radiation amount with which the plant is irradiated, a sap flow sensor that measures a flow rate of sap flowing in a body of the plant, and an absorbed nutrient sensor that measures a nutritional state of the plant.

19 Claims, 6 Drawing Sheets

(56) References Cited

U.S. PATENT DOCUMENTS

| | | | |
|---|---|---|---|
| 7,437,928 B2* | 10/2008 | Bos | G01F 15/18 |
| | | | 73/204.22 |
| 9,107,354 B2* | 8/2015 | Martin | A01G 25/167 |
| 10,871,480 B2* | 12/2020 | Miresmailli | A01G 25/16 |
| 11,143,534 B2* | 10/2021 | Lee | G01N 33/0098 |
| 2009/0025287 A1 | 1/2009 | Lee | |
| 2019/0170718 A1 | 7/2019 | Miresmailli et al. | |
| 2019/0204131 A1* | 7/2019 | Jablokov | F24C 3/122 |

FOREIGN PATENT DOCUMENTS

| | | | |
|---|---|---|---|
| CN | 106643912 A | | 5/2017 |
| CN | 109655121 A | | 4/2019 |
| JP | 6478116 B2 | | 3/1989 |
| JP | H08103173 A | | 4/1996 |
| JP | 2016065868 A | | 4/2016 |
| JP | 2019109104 A | * | 7/2019 |
| WO | 2019188848 A1 | | 10/2019 |

OTHER PUBLICATIONS

International Search Report for International Application No. PCT/JP2020/040639; Date of Mailing, Jan. 19, 2021.
PCT Written Opinion of the International Searching Authority for corresponding PCT/JP2020/040639; Date of Mailing, Jan. 19, 2021.
EPO Extended European Search Report corresponding to EP Application No. 20881104.2; Mailing Date, Oct. 24, 2023.

* cited by examiner

PLANT BIOSENSOR

CROSS REFERENCE TO RELATED APPLICATIONS

This is the U.S. national stage of application No. PCT/JP2020/040639, filed on Oct. 29, 2020. Priority under 35 U.S.C. § 119(a) and 35 U.S.C. § 365(b) is claimed from Japanese Application No. 2019-200153, filed Nov. 1, 2019, the disclosure of which is also incorporated herein by reference.

TECHNICAL FIELD

The present disclosure relates to a plant biosensor capable of measuring environmental information and biological information of a plant.

BACKGROUND ART

Patent Document 1 discloses an environment control method for a greenhouse.

PRIOR ART DOCUMENTS

Patent Documents

Patent Document 1: JP H08-103173 A

SUMMARY OF THE INVENTION

Problems to be Solved by the Invention

With the environment control method, various devices for adjusting the environment in a greenhouse are controlled based on light intensity, temperature, and humidity, which are environmental information in the greenhouse. For this reason, there is a case of not being capable of providing an optimal environment for individual plants in the greenhouse.

An object of the present disclosure is to provide a plant biosensor capable of measuring environmental information and biological information of a plant.

Means for Solving the Problems

A plant biosensor of an example of the present disclosure is
a plant biosensor that measures environmental information and biological information of a plant, the plant biosensor including:
a solar radiation sensor that measures a solar radiation amount with which the plant is irradiated;
a sap flow sensor that measures a flow rate of sap flowing in a body of the plant; and
an absorbed nutrient sensor that measures a nutritional state of the plant.

Here, "environmental information" is information regarding the environment of a measurement object plant, and includes a solar radiation amount, a carbon dioxide amount, humidity, temperature, and a volatile organic compound amount. "Biological information" is information regarding biological information of a measurement object plant and includes a flow rate of sap and a nutritional state. "Nutritional state" is indicated by, for example, the ingredient amount of a predetermined substance in the body of a plant. The predetermined substance includes nitrate nitrogen, carbohydrates, proteins, minerals, antioxidants, and moisture.

Effects of the Invention

The plant biosensor includes the solar radiation sensor that measures the solar radiation amount with which the plant is irradiated, the sap flow sensor that measures the flow rate of sap flowing in the body of the plant, and the absorbed nutrient sensor that measures a nutritional state of the plant. Such configuration makes it possible to achieve a plant biosensor capable of measuring biological information of individual plants in a greenhouse, for example.

MODE FOR CARRYING OUT THE INVENTION

An example of the present disclosure will be described below with reference to the accompanying drawings. In the following description, terms indicating specific directions or positions (e.g., terms including "up", "down", "right", and "left") are used as necessary, but these terms are used for facilitating understanding of the present disclosure with reference to the drawings, and the technical scope of the present disclosure is not limited by the meanings of these terms. The following description is merely exemplary in nature, and is not intended to limit the present disclosure, its application, or its use. Furthermore, the drawings are schematic, and ratios of dimensions and the like do not necessarily match actual ones.

Figure 1:
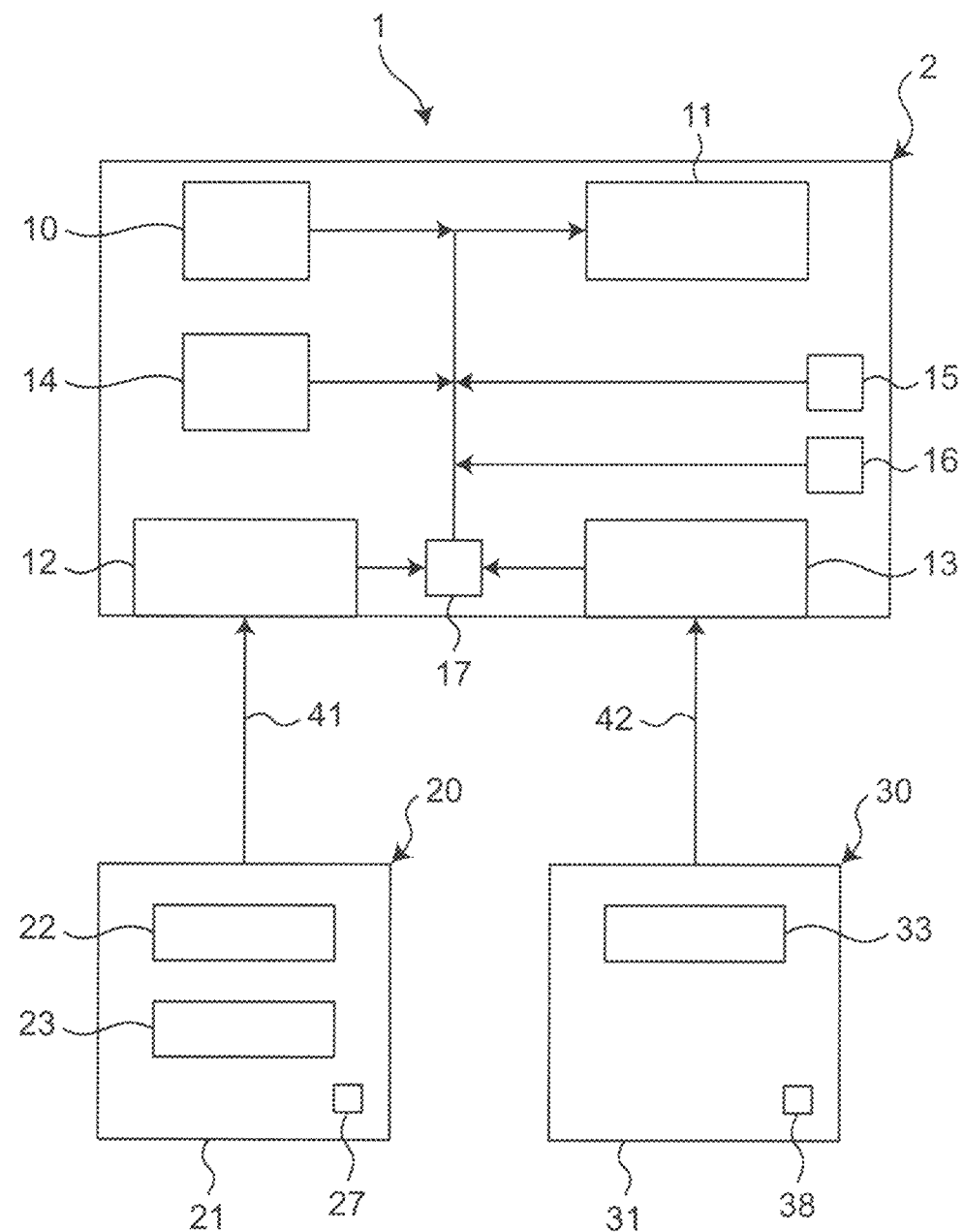
FIG. 1 is a block diagram showing a configuration of a plant biosensor of one embodiment of the present disclosure.

As shown in FIG. 1, a plant biosensor 1 of one embodiment of the present disclosure includes a solar radiation sensor 10, a sap flow sensor 20, and an absorbed nutrient sensor 30, and measures environmental information and biological information of a measurement object plant.

The plant biosensor 1 further includes a casing 2 (hereinafter referred to as a first casing 2) as an example, and the solar radiation sensor 10 is accommodated inside the casing 2. Specifically, a substrate (not illustrated) is provided inside the first casing 2, and this substrate is mounted with the solar radiation sensor 10, a communication device 11, a first connection part 12, a second connection part 13, a carbon dioxide sensor 14, a temperature and humidity sensor 15, a VOC sensor 16, and an arithmetic device 17 (an example of a calculation unit). The solar radiation sensor 10 and the communication device 11 are disposed at one end (e.g., the upper end shown in FIG. 1) of the first casing 2, and the first connection part 12 and the second connection part 13 are disposed at the other end (e.g., the lower end shown in FIG. 1) opposing the one end of the first casing 2.

The solar radiation sensor 10 measures a solar radiation amount with which a measurement object plant is irradiated. Specifically, the solar radiation sensor 10 measures a solar radiation amount with which the periphery of a measurement object plant is irradiated and measures this solar radiation amount as the solar radiation with which the plant is irradiated.

The communication device 11 receives information regarding a measurement result measured by sensors including the solar radiation sensor 10, the sap flow sensor 20, and the absorbed nutrient sensor 30, and transmits the received information regarding a measurement result to an external device connected wirelessly or by wire. In a case where information regarding the received measurement result is wirelessly transmitted, any communication standard such as Wi-Fi (brand name) and Bluetooth (registered trademark) can be used.

The first connection part 12 is connected with the sap flow sensor 20 and receives information regarding a measurement result measured by the sap flow sensor 20. The first connection part 12 and the sap flow sensor 20 are connected by, for example, an electrical cable 41. The second connection part 13 is connected with the absorbed nutrient sensor 30 and receives information regarding a measurement result measured by the absorbed nutrient sensor 30. The second connection part 13 and the absorbed nutrient sensor 30 are connected by, for example, an optical fiber 42. The first connection part 12 and the sap flow sensor 20 may be connected by wireless communication of any communication standard.

The carbon dioxide sensor 14 measures a carbon dioxide amount in the air around a measurement object plant. The temperature and humidity sensor 15 measures a temperature and humidity around a measurement object plant. The VOC sensor 16 measures a volatile organic compound amount in the air around a measurement object plant.

The arithmetic device 17 includes a CPU that performs arithmetic operation, a ROM and a RAM that store information, and the like, and calculates a reproductive growth degree of the plant based on a photosynthesis amount of the plant measured by a flow rate measurement unit 27 described later and a vegetative growth degree of the plant measured by a growth degree measurement unit 38 described later. A photosynthesis amount of the plant measured by the flow rate measurement unit 27 is acquired from the sap flow sensor 20 via the first connection part 12. A vegetative growth degree of the plant measured by the growth degree measurement unit 38 is acquired from the absorbed nutrient sensor 30 via the second connection part 13.

"Vegetative growth degree" is a degree indicating the growth state of a trunk, a branch, a stem, a leaf, and the like. "Reproductive growth degree" is a degree indicating the growth state of a flower, a bud, a fruit, and the like.

As an example, the various sensors, the communication device 11, and the arithmetic device 17 that constitute the plant biosensor 1 are electrically connected to a battery (not illustrated) accommodated inside the first casing 2, and electric power is supplied from the battery.

Figure 2:
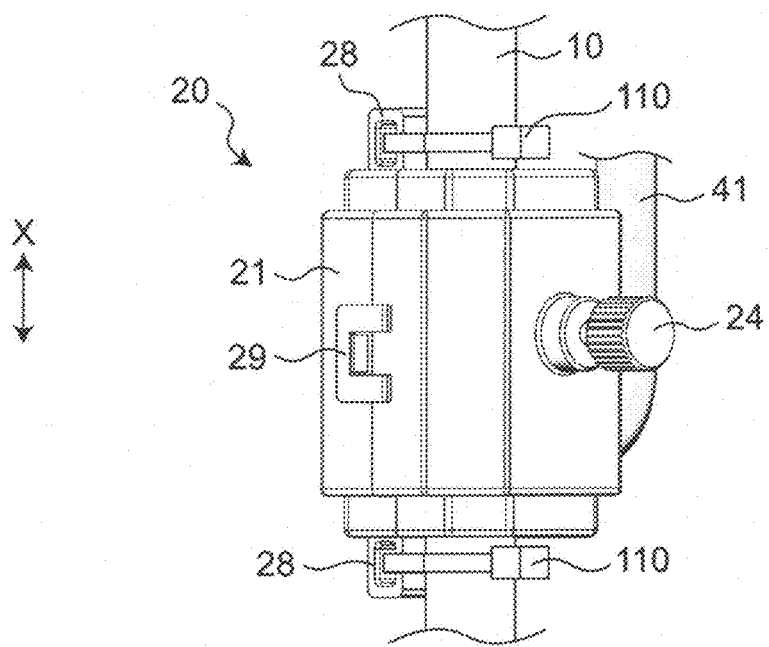
FIG. 2 is a perspective view showing a sap flow sensor of the plant biosensor of FIG. 1.
Figure 3:
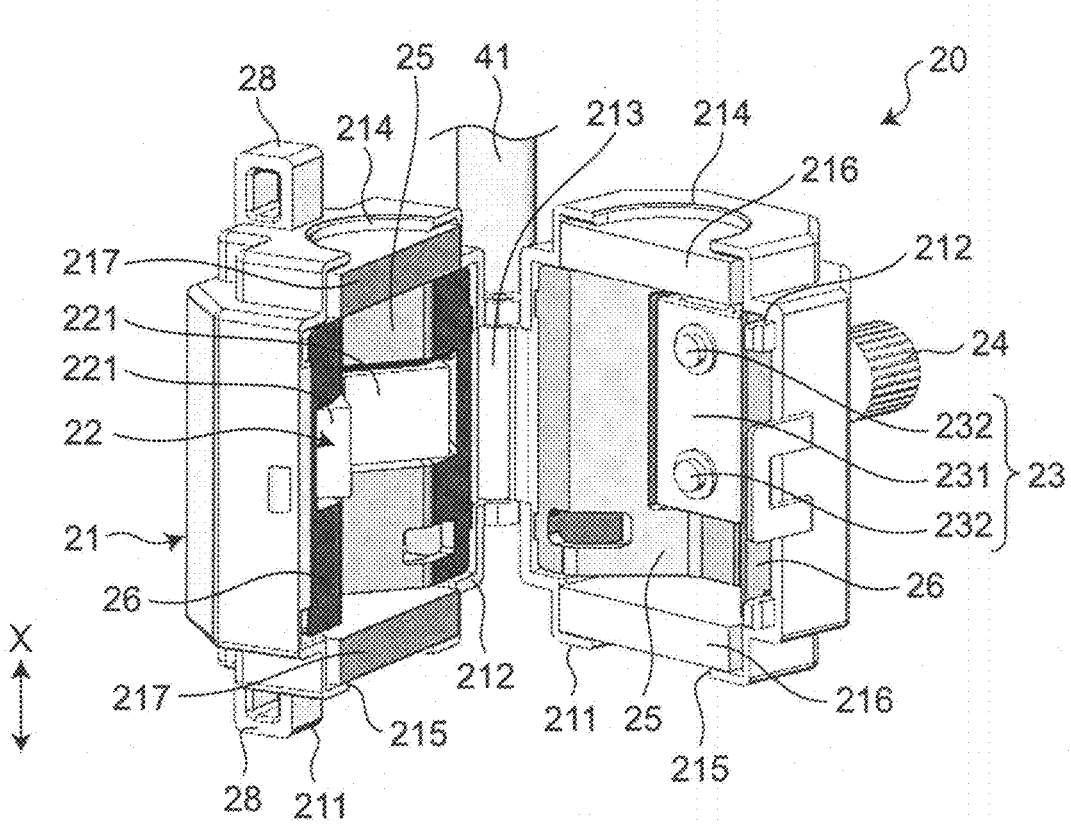
FIG. 3 is a perspective view showing a state in which a second casing of the sap flow sensor of FIG. 2 is opened.
Figure 4:
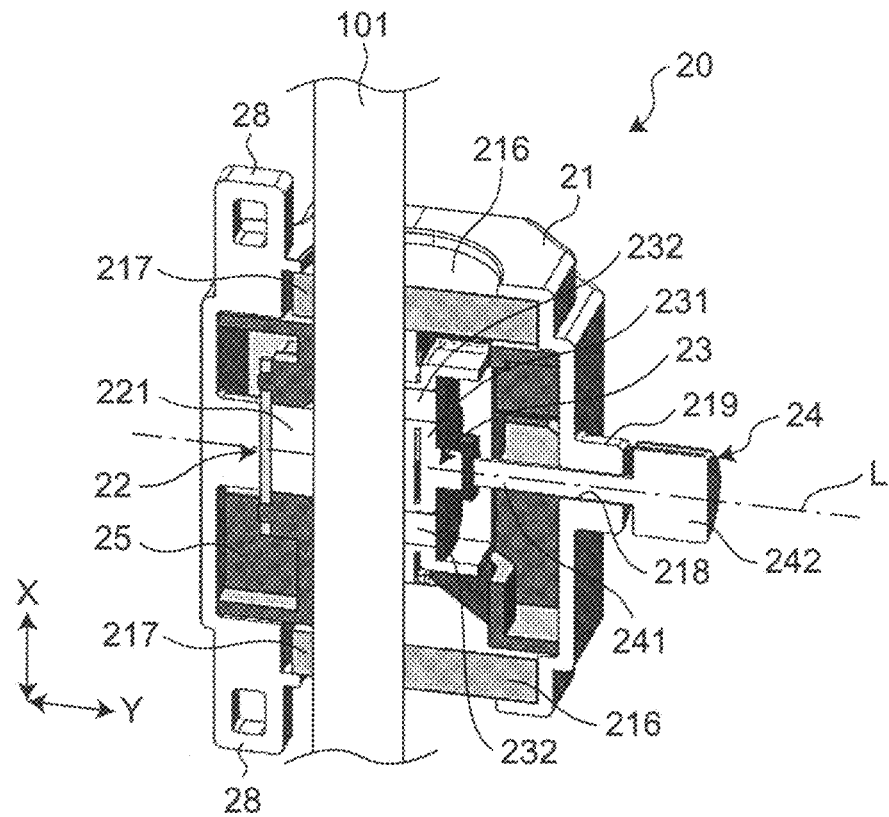
FIG. 4 is a first cross-sectional view of the sap flow sensor of FIG. 2.
Figure 5:
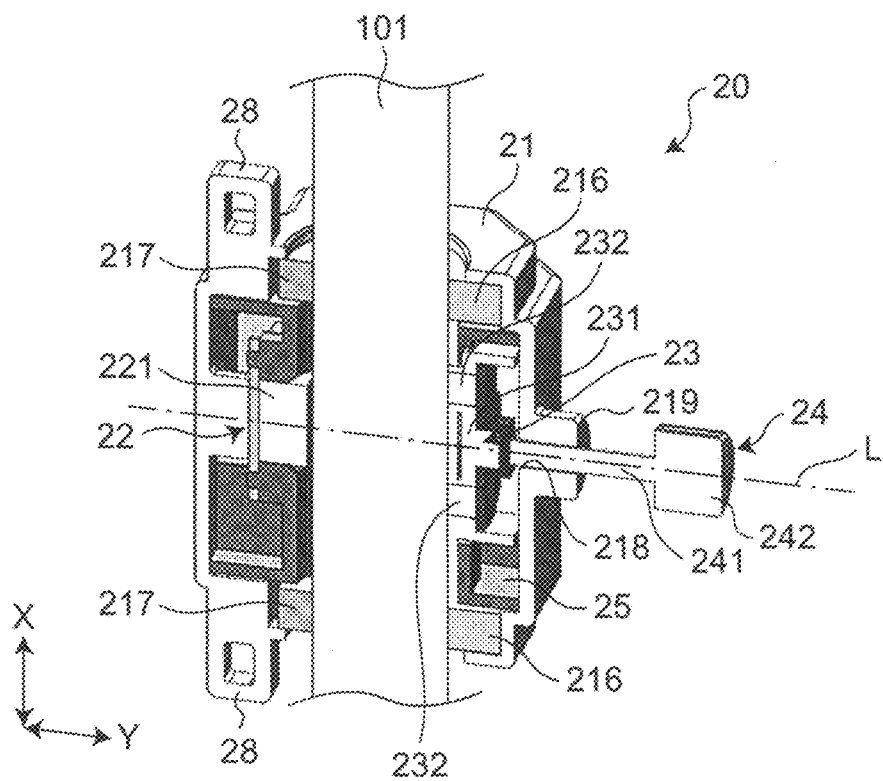
FIG. 5 is a second cross-sectional view of the sap flow sensor of FIG. 2.

As shown in FIG. 2 to FIG. 5, the sap flow sensor 20 includes a casing 21 (hereinafter referred to as a second casing 21) inside of which is provided with an accommodation part 25, and a heater unit 22 and a temperature sensor unit 23 disposed inside the accommodation part 25. In this sap flow sensor 20, as an example, as shown in FIG. 4 and FIG. 5, the heater unit 22 and the temperature sensor unit 23 are disposed so as to face each other across a main stem 101 in the radial direction (e.g., the Y direction shown in FIG. 4 and FIG. 5) of the main stem 101 in a state where the second casing 21 is attached to the main stem 101 (an example of a first structure part through which sap flows).

As shown in FIG. 2, the second casing 21 has a substantially rectangular parallelepiped box shape and is configured to be attachable about a direction (e.g., the X direction) in which the main stem 101 extends with respect to the main stem 101 of a measurement object plant. Specifically, as shown in FIG. 3, the second casing 21 includes two members 211 rotatably connected via a hinge 213. Each member 211 has an opening surface 212, and the members 211 are connected with each other in a state where the opening surfaces 212 oppose each other. The hinge 213 extends in a long direction of the second casing 21 and is disposed on one side edge in a short direction of the opening surface 212 of each member 211. As shown in FIG. 1, the other side surface in the short direction at the opening surface 212 of the second casing 21 is provided with a connection mechanism 29 for snap-fitting each member 211.

As shown in FIG. 3, the surface (in other words, the inner surface of the second casing 21) of the accommodation part 25 is provided with a heat insulation layer 26. The heat insulation layer 26 includes a closed space (air or vacuum) or a material having a high heat insulation property (e.g., sponge). By providing the heat insulation layer 26, it is possible to efficiently apply heat to the main stem 101 without releasing heat to the outside of the accommodation part 25, and it is possible to secure heat insulation between the heater unit 22 and the temperature sensor unit 23. As an example, the heat insulation layer 26 is provided on the entire surface of the accommodation part 25 except for the heater unit 22, the temperature sensor unit 23, and a pair of through holes 214 and 215 described later.

As shown in FIG. 3, the second casing 21 includes the pair of through holes 214 and 215 (an example of a pair of first through holes) provided at both respective ends in a first direction (e.g., the X direction) in which the main stem 101 extends in the state where the second casing 21 is attached to the main stem 101, and a pair of elastic members 216 and 217 (an example of a pair of first elastic members) provided in the through holes 214 and 215, respectively.

Each of the through holes 214 and 215 has a substantially circular shape in which the main stem 101 can be disposed and penetrates the second casing 21 in the X direction. Each of the elastic members 216 and 217 is made of, for example, sponge, and is disposed on each member 211 constituting the second casing 21. In other words, the elastic members 216 and 217 are each disposed so as to be able to hold the main stem 101 from a radial direction (in other words, a second direction intersecting the first direction) of the main stem 101 in the state where the second casing 21 is attached to the main stem 101. The elastic members 216 and 217 prevent the sap flow sensor 20 from falling off a measurement object plant.

Both ends of the second casing 21 in the X direction are each provided with a band attachment part 28 for attaching a banding band 110. By connecting the second casing 21 and the main stem 101 using the banding band 110, it is possible to more reliably prevent the sap flow sensor 20 from falling off a measurement object plant.

As shown in FIG. 3, the heater unit 22 is disposed inside the accommodation part 25 in such a manner to be able to heat the main stem 101. Specifically, the heater unit 22 has a substantially V shape including a first surface and a second surface disposed to intersect the first surface. As shown in FIG. 3, each of the first surface and the second surface is provided with a heat transfer sheet 221. In other words, the heater unit 22 is configured such that each of the first surface and the second surface is in contact with the main stem 101 via the heat transfer sheet 221.

As shown in FIG. 3, the temperature sensor unit 23 is disposed inside the accommodation part 25 so as to be able to measure the temperature of the sap flowing through the main stem 101 on both sides with respect to the heater unit 22 in a direction (e.g., the X direction) where the main stem 101 extends in the state where the second casing 21 is attached to the main stem 101. Specifically, the temperature sensor unit 23 includes a main body unit 231 having a rectangular plate shape in which the X direction is a long direction, and a pair of temperature sensors 232 provided on a surface of the main body unit 231 opposing the heater unit 22. Each temperature sensor 232 has a substantially cylindrical shape protruding from the main body unit 231 toward the heater unit 22 and is disposed at an interval in the X direction. A tip of each temperature sensor 232 comes into contact with the main stem 101 and measures a temperature of the sap flowing through the main stem 101.

As shown in FIG. 3, the sap flow sensor 20 includes a position adjustment mechanism 24. As shown in FIGS. 4 and 5, the position adjustment mechanism 24 includes a screw hole 218 provided in the second casing 21 and a position adjustment member 241.

The screw hole 218 has a shape that allows the position adjustment member 241 to be inserted, is disposed on a straight line L passing through the heater unit 22 and the temperature sensor unit 23 in the second casing 21, and penetrates the second casing 21 in a direction (e.g., the Y direction) in which the straight line L extends. An inner periphery of the screw hole 218 is provided with a screw groove (not illustrated). The straight line L extends along the radial direction of the main stem 101 in the state where the second casing 21 is attached to the main stem 101. An outer peripheral surface of the second casing 21 in the direction where the straight line L extends is provided with a boss part 219. The screw hole 218 penetrates this boss part 219 in the direction where the straight line L extends.

As an example, the position adjustment member 241, which has an elongated substantially cylindrical shape, extends from the outside of the accommodation part 25 to the inside of the accommodation part 25 via the screw hole 218, and is connected to the main body unit 231 of the temperature sensor unit 23. An outer periphery of the position adjustment member 241 is provided with a screw thread (not illustrated) to be fitted into the screw groove of the screw hole 218. The position adjustment member 241 is configured to be movable in a direction where the straight line L extends by being rotated about the straight line L. In other words, by rotating the position adjustment member 241 about the straight line L, it is possible to move the temperature sensor unit 23 in the direction where the straight line L extends (see FIG. 4 and FIG. 5) to perform position adjustment. An end of the position adjustment member 241 on the outer side of the accommodation part 25 is provided with a substantially cylindrical operation unit 242 having a diameter larger than the screw hole 218. This operation unit 242 facilitates rotation operation of the position adjustment member 241.

As shown in FIG. 1, the sap flow sensor 20 further includes the flow rate measurement unit 27. The flow rate measurement unit 27 includes a CPU that performs arithmetic operation, a ROM and a RAM that store information, and a communication device that transmits information to the first connection part 12 and measures a flow rate of the sap flowing through inside the body of the main stem 101 based on a temperature of the sap flowing through inside the body of the main stem 101 measured by the temperature sensor unit 23. The flow rate measurement unit 27 measures a photosynthesis amount performed by a plant from a measured flow rate of sap. That is, the flow rate measurement unit 27 is an example of a first measurement unit. Information regarding a result measured by the sap flow sensor 20 is transmitted to the first connection part 12 via the electrical cable 41.

As an example, each of the heater unit 22, the temperature sensor unit 23, and the flow rate measurement unit 27 is electrically connected to a battery (not illustrated) accommodated inside the second casing 21, and electric power is supplied from the battery.

As shown in FIG. 6 to FIG. 9, the absorbed nutrient sensor 30 includes a casing 31 (hereinafter referred to as a third casing 31), and a holding part 32 and a nutritional state sensor unit 33 that are provided inside the third casing 31.

Figure 6:
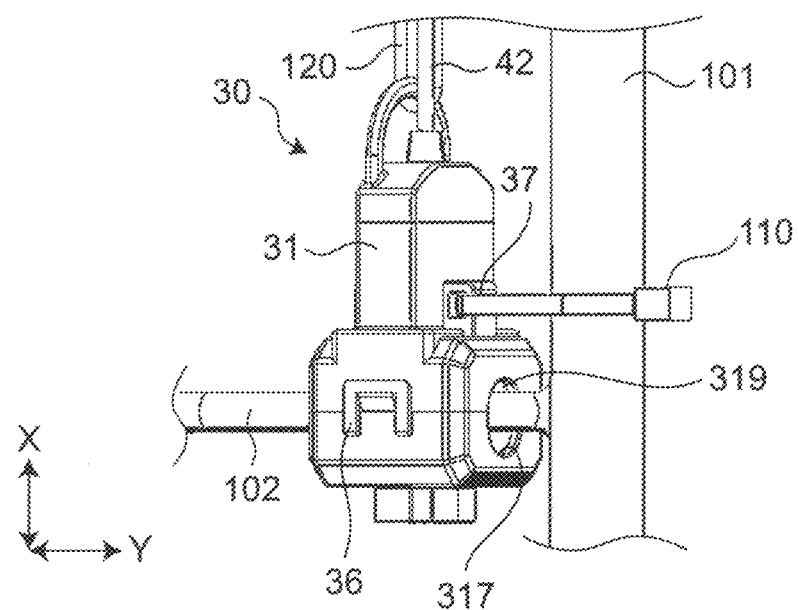
FIG. 6 is a perspective view showing an absorbed nutrient sensor of the plant biosensor of FIG. 1.

As shown in FIG. 6, the third casing 31 is configured to be attachable about a direction (e.g., the Y direction) in which a petiole 102 (an example of a second structure part through which sap flows) extends with respect to the petiole 102 of the plant. As an example, the petiole 102 extends in a direction (e.g., the X direction) intersecting a direction in which the main stem 101 extends.

Figure 7:
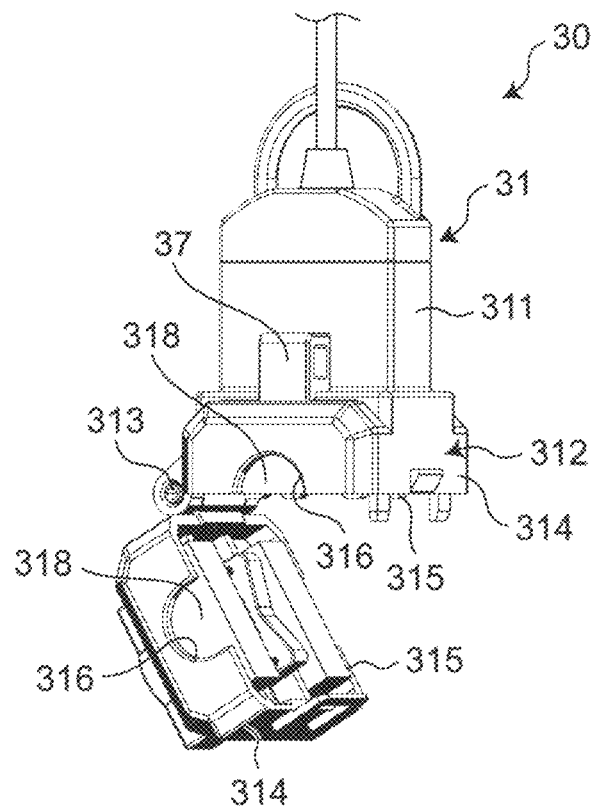
FIG. 7 is a perspective view showing a state in which a third casing of the absorbed nutrient sensor of FIG. 6 is opened.
Figure 8:
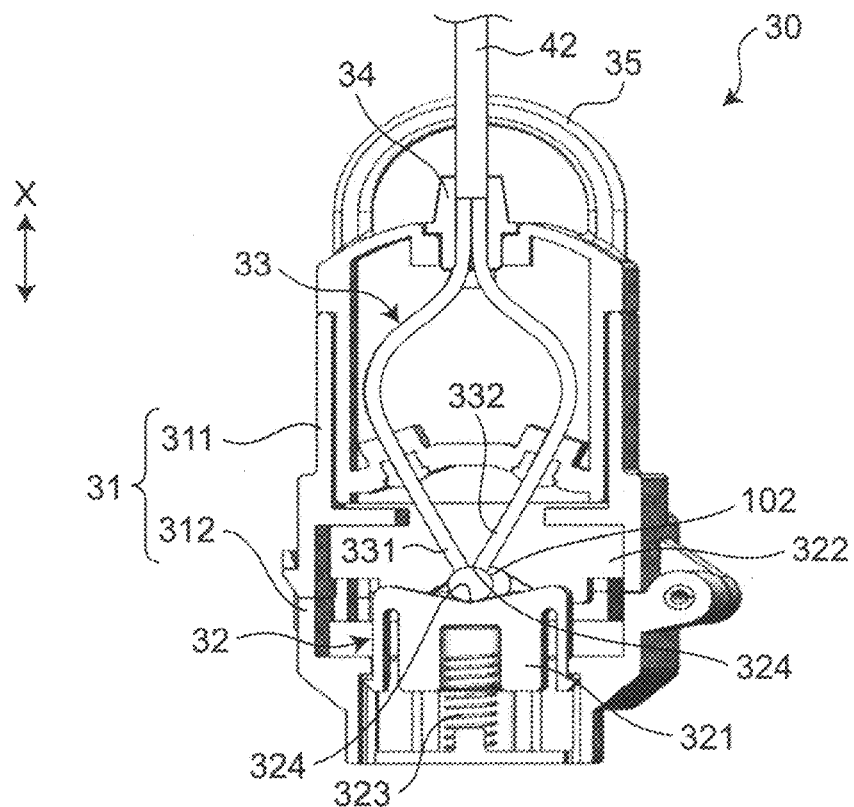
FIG. 8 is a first cross-sectional view of the absorbed nutrient sensor of FIG. 6.
Figure 9:
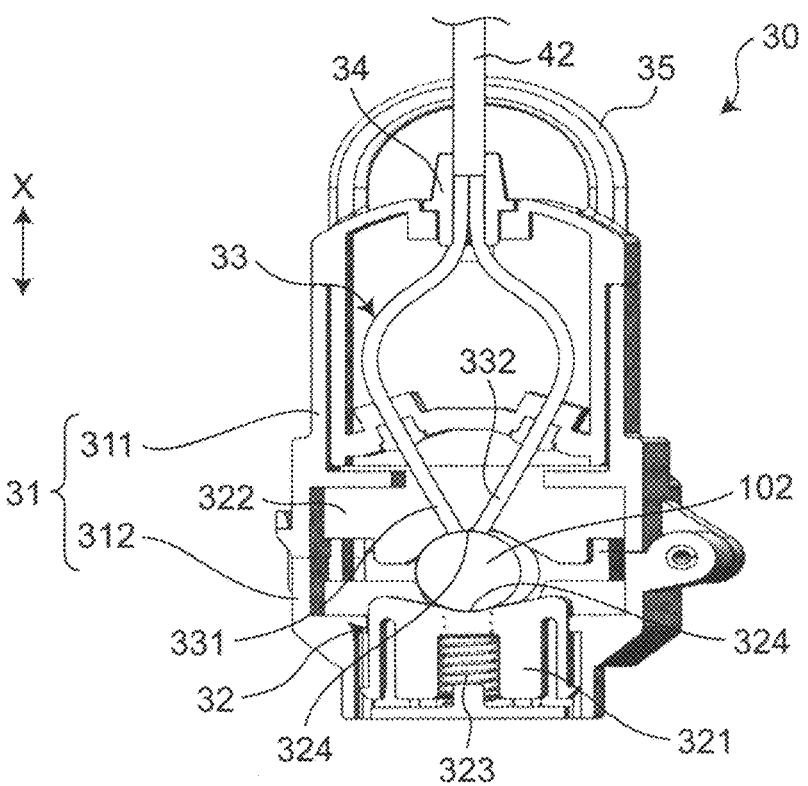
FIG. 9 is a second cross-sectional view of the absorbed nutrient sensor of FIG. 6.

Specifically, the third casing 31, as shown in FIG. 6 and FIG. 7, has a substantially T shape as a whole, and, as shown in FIG. 8 and FIG. 9, includes a first member 311 in which the holding part 32 is accommodated and a second member 312 in which the nutritional state sensor unit 33 is accommodated.

The first member 311 has a substantially rectangular plate shape, and the second member 312 is connected to one end of the first member 311 in the long direction. The other end of the first member 311 in the long direction is provided with a connection part 34 to which the optical fiber 42 is connected, and a substantially arc-shaped cable attachment part 35 to which a cable 120 (see FIG. 1) for hanging the absorbed nutrient sensor 30 is attached. The second member 312 has a substantially rectangular parallelepiped box shape and is disposed such that the short direction of the first member 311 becomes the long direction of the second member 312. The second member 312 includes two members 314 rotatably connected via a hinge 313. Each member 314 includes an opening surface 315. The members are connected in a state where the opening surfaces 315 oppose each other. The hinge 313 extends in the long direction of the third casing 31 and is disposed on one side edge in the short direction of the opening surface 315 of each member 314. As shown in FIG. 6, the other side surface in the short direction at the opening surface 315 of the third casing 31 is provided with a connection mechanism 36 for snap-fitting each member 314.

As shown in FIG. 6 and FIG. 7, the second member 312 includes a pair of through holes 316 and 317 (an example of a pair of second through holes) provided at both ends in a direction (e.g., the Y direction) in which the petiole 102 extends in a state where the third casing 31 is attached to the petiole 102, and a pair of elastic members 318 and 319 (an example of a pair of second elastic members) provided in the through holes 316 and 317, respectively.

Each of the through holes 316 and 317 has a substantially circular shape in which the petiole 102 can be disposed and penetrates the third casing 31 in the Y direction. Each of the elastic members 318 and 319 is made of, for example, sponge, and is disposed on each member 314 constituting the second member 312. In other words, the elastic members 318 and 319 are each disposed so as to be able to hold the petiole 102 from the radial direction of the petiole 102 in the state where the third casing 31 is attached to the petiole 102. The elastic members 318 and 319 prevent the absorbed nutrient sensor 30 from falling off a measurement object plant.

As shown in FIG. 6 and FIG. 7, the surface of the second member 312 to which the first member 311 is connected is provided with a band attachment part 37 for attaching the banding band 110. By connecting the second member 312 and the main stem 101 using the banding band 110, it is possible to more reliably prevent the absorbed nutrient sensor 30 from falling off a measurement object plant.

As shown in FIG. 8 and FIG. 9, the holding part 32 includes a first holding member 321, a second holding member 322 disposed so as to oppose the first holding member 321, and a biasing member 323 that biases the first holding member 321 toward the second holding member 322. The first holding member 321 is disposed to be movable in a radial direction (in other words, a fourth direction (e.g., the X direction) intersecting the third direction in which the petiole 102 extends in the state of being attached to the petiole 102) of the petiole 102 in the state where the third casing 31 is attached to the petiole 102. The second holding member 322 is disposed so as to oppose the first holding member 321 in the X direction and is fixed to the third casing 31. The biasing member 323 include, for example, a coil spring, and is disposed between the first holding member 321 and the bottom surface of the third casing 31 on the second member 312 side in the X direction.

Each of the first holding member 321 and the second holding member 322 includes a recess 324 that is recessed in a direction away from each other and in which the petiole 102 is disposed. Each recess 324 is curved along the outer shape of the petiole 102.

As an example, the nutritional state sensor unit 33 includes a light-projecting unit 331 that irradiates a measurement site of a plant with light and a light-receiving unit 332 that receives light from a measurement site of the plant. This nutritional state sensor unit 33 measures a nutritional state of the petiole 102 (an example of a measurement site) from light received by the light-receiving unit 332. The light-projecting unit 331 includes, for example, a light-emitting diode (an example of a light-emitting element that generates light) having a small warm-up time and high time responsiveness, and a light-projecting fiber that guides light generated by the light-emitting diode to the petiole 102. The light-projecting unit 331 can also include a plurality of light-emitting diodes having different wavelengths. The light-receiving unit 332 includes, for example, a spectrometer or a photodiode (an example of a light-receiving element) that receives reflected light emitted from the light-emitting diode to the petiole 102 and reflected, and a light-receiving fiber that guides the reflected light from the petiole 102 to the spectrometer or the photodiode. As an example, the light-projecting unit 331 and the light-receiving unit 332 are disposed on the same side (in FIG. 8 and FIG. 9, above the petiole 102) with respect to the petiole 102 in a state where the third casing 31 is attached in plan view including the third direction and the fourth direction (see FIG. 8 and FIG. 9). The light-projecting fiber and the light-receiving fiber are disposed in a V shape.

As shown in FIG. 1, the absorbed nutrient sensor 30 further includes the growth degree measurement unit 38 as an example of a second measurement unit. The growth degree measurement unit 38 includes a CPU that performs arithmetic operation, a ROM and a RAM that store information, and a communication device that transmits information to the second connection part 13 and measures a vegetative growth degree of a measurement object plant based on a nutritional state of the petiole 102 measured by the nutritional state sensor unit 33. Information regarding a result measured by the absorbed nutrient sensor 30 is transmitted to the second connection part 13 via the optical fiber 42.

Each of the nutritional state sensor unit 33 and the growth degree measurement unit 38 is electrically connected to a battery (not illustrated) accommodated inside the third casing 31, and electric power is supplied from the battery.

Figure 10:
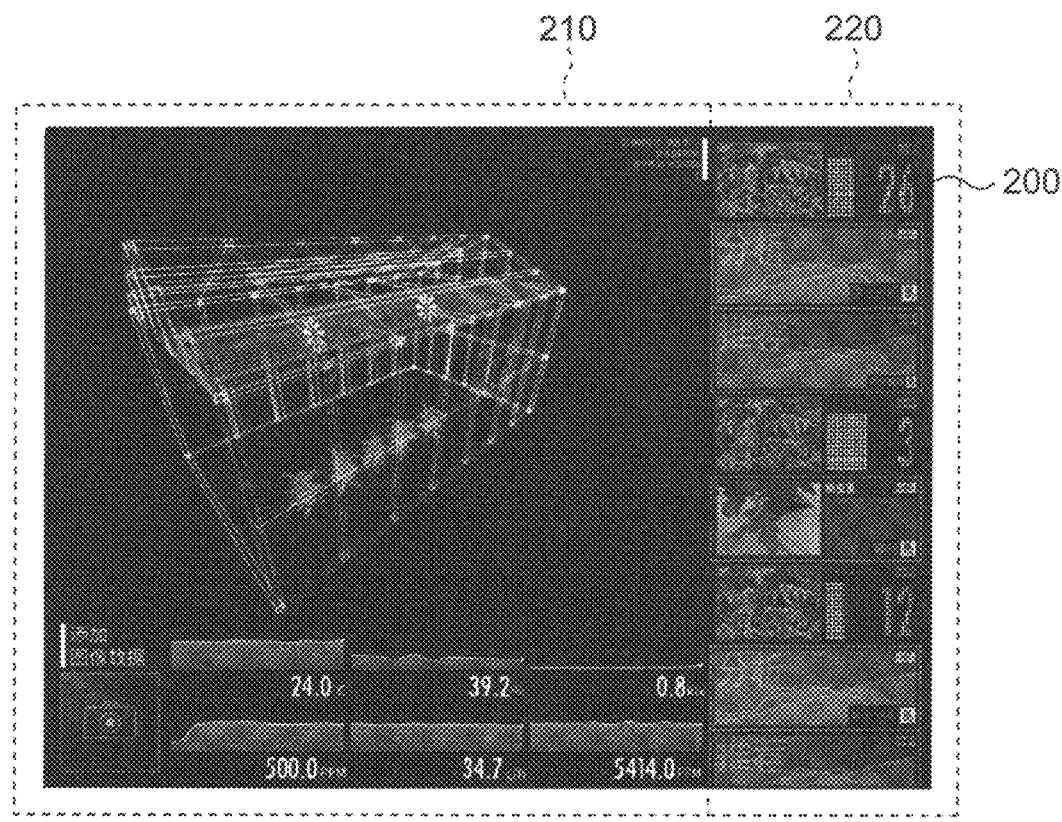
FIG. 10 is a first view for explaining a usage example of information measured by the plant biosensor of FIG. 1.
Figure 11:
FIG. 11 is a second view for explaining the usage example of information measured by the plant biosensor of FIG. 1.

With reference to FIG. 10 and FIG. 11, a usage example of environmental information and biological information of a plant measured by the plant biosensor 1 will be described. An image 200 shown in FIG. 10 includes a first display region 210 and a second display region 220. An upper region of the first display region 210 displays CG of a greenhouse, and a lower region of the first display region 210 displays in real time environmental information and biological information of a plant measured by the plant biosensor 1. The second display region 220 displays recommendation regarding cultivation management of a plant in chronological order from environmental information and biological information of a plant measured and accumulated by the plant biosensor 1. An image 300 shown in FIG. 11 is an example of recommendation. An upper region 310 of the image 300 displays content of the recommendation, and a lower region 320 of the image 300 displays environmental information and biological information of a plant that are the basis for the displayed recommendation.

According to the plant biosensor 1, the following advantageous effects can be achieved.

It includes the solar radiation sensor 10 that measures the solar radiation amount with which the plant is irradiated, the sap flow sensor 20 that measures the flow rate of sap flowing in a body of the plant, and the absorbed nutrient sensor 30 that measures a nutritional state of the plant. Such configuration makes it possible to achieve the plant biosensor 1 capable of measuring biological information of individual plants in a greenhouse, for example.

The solar radiation sensor 10 and the communication device 11 are disposed at one end of the first casing 2, and the first connection part 12 and the second connection part 13 are disposed at the other end of the first casing 2 opposing the one end of the first casing 2. Such configuration makes it possible to dispose the solar radiation sensor 10 and the communication device 11 at the upper end of the first casing 2 in the vertical direction at the time of use of the plant biosensor 1, for example. In this case, it is possible to more reliably transmit the measured environmental information and biological information of a plant to the external device while more accurately measuring a solar radiation amount with which the measurement object plant is irradiated.

The carbon dioxide sensor 14, the temperature and humidity sensor 15, and the VOC sensor 16 are included.

Such configuration makes it possible to achieve the plant biosensor 1 capable of measuring environmental information of more plants.

The sap flow sensor 20 includes the second casing 21, the heater unit 22, the temperature sensor unit 23, and the flow rate measurement unit 27. The second casing 21 internally includes the accommodation part 25 provided with the heat insulation layer 26 on the surface thereof and is configured to be attachable around the direction in which the main stem 101 extends with respect to the main stem 101. The heater unit 22 is disposed inside the accommodation part 25 and configured to be able to heat the main stem 101. The temperature sensor unit 23 is disposed inside the accommodation part 25 and is configured to be able to measure the temperature of the sap flowing through the main stem 101 on both sides with respect to the heater unit 22 in the direction where the main stem 101 extends in the state where the second casing 21 is attached to the main stem 101. The flow rate measurement unit 27 measures a flow rate of the sap flowing through inside the body of the main stem 101 based on a temperature of the sap flowing through inside the body of the main stem 101 measured by the temperature sensor unit 23. Such configuration makes it possible to more accurately measure a flow rate of sap flowing in a body of the plant.

The heater unit 22 and the temperature sensor unit 23 are disposed so as to face each other across the main stem 101 in the radial direction of the main stem 101 in the state where the second casing 21 is attached to the main stem 101. With such configuration, the heat of the heater unit 22 is not directly transmitted to the temperature sensor unit 23, the SN ratio of the sap flow sensor 20 can be increased. Space efficiency in the accommodation part 25 can be enhanced.

The sap flow sensor 20 includes the position adjustment member 241. The position adjustment member 241 extends from the outside of the accommodation part 25 to the inside of the accommodation part 25 via the screw hole 218, is connected to the temperature sensor unit 23, is provided with the screw thread fitted into the screw groove on the outer periphery, and is configured to be movable in the direction where the straight line L extends by being rotated about the straight line L. Such configuration makes it possible to allow the sap flow sensor 20 to be attached to the main stem 101 without damaging the main stem 101 even when the measurement object plant grows and the main stem 101 becomes large.

The heater unit 22 includes the first surface that can come into contact with the main stem 101 and the second surface that is disposed so as to intersect the first surface and can come into contact with the main stem 101. Each of the first surface and the second surface is provided with the heat transfer sheet 221 including elasticity, and each of the first surface and the second surface comes into contact with the main stem 101 via the heat transfer sheet 221. Such configuration makes it possible to stably bring the heater unit 22 into contact with the main stem 101, and therefore makes it possible to more accurately measure a flow rate of sap flowing in a body of the plant.

The second casing 21 includes a pair of first elastic members 216 and 217 provided in each of the pair of first through holes 214 and 215 and capable of holding the main stem 101 in the radial direction of the main stem 101. Such configuration makes it possible to allow the sap flow sensor 20 to be attached to the main stem 101 without damaging the main stem 101. The first elastic members 216 and 217 may be provided in only one of the pair of first through holes 214 and 215.

The absorbed nutrient sensor 30 includes the third casing 31, the holding part 32, and the nutritional state sensor unit 33. The third casing 31 is configured to be attachable around the direction in which the petiole 102 extends with respect to the petiole 102 of the plant. The holding part 32 is provided inside the third casing 31 and is configured to be able to hold the petiole 102 in the radial direction of the petiole 102. The nutritional state sensor unit 33 is provided inside the third casing 31 and is configured to be able to measure a nutritional state of the petiole 102. Such configuration makes it possible to more accurately measure a nutritional state of the plant.

The holding part 32 includes the first holding member 321, the second holding member 322, and the biasing member 323. The first holding member 321 is disposed to be movable along the radial direction of the petiole 102 in the state where the third casing 31 is attached to the petiole 102. The second holding member 322 is disposed so as to oppose the first holding member 321 in the radial direction of the petiole 102 in the state where the third casing 31 is attached to the petiole 102 and is fixed to the third casing 31. The biasing member 323 is configured to be capable of biasing the first holding member 321 in a direction approaching the second holding member 322. With such configuration, even when an external force is applied to the petiole 102, the petiole 102 can be retained at a predetermined measurement position, and therefore a nutritional state of the plant can be more reliably measured.

Each of the first holding member 321 and the second holding member 322 has the recess 324 that is recessed in the direction away from each other and in which the petiole 102 is disposed. With such configuration, a position of the petiole 102 with respect to the holding part 32 can be determined more accurately, and therefore a nutritional state of the plant can be more reliably measured.

The third casing 31 includes a pair of second elastic members 318 and 319 provided in each of the pair of second through holes 316 and 317 and capable of holding the petiole 102 in the radial direction of the petiole 102. Such configuration makes it possible to allow the absorbed nutrient sensor 30 to be attached to the petiole 102 without damaging the petiole 102. The second elastic members 318 and 319 may be provided in only one of the pair of second through holes 316 and 317.

The plant biosensor 1 further includes the first measurement unit (e.g., the flow rate measurement unit 27), the second measurement unit (e.g., the growth degree measurement unit 38), and the calculation unit (e.g., the arithmetic device 17). The flow rate measurement unit 27 measures a photosynthesis amount performed by the plant from a flow rate of sap measured by the sap flow sensor 20. The growth degree measurement unit 38 measures a vegetative growth degree of the plant from a nutritional state of the plant measured by the absorbed nutrient sensor 30. The arithmetic device 17 calculates a reproductive growth degree of the plant based on a photosynthesis amount of the plant measured by the flow rate measurement unit 27 and a vegetative growth degree of the plant measured by the growth degree measurement unit 38. With such configuration, a growth state of the plant can be grasped in real time.

The plant biosensor 1 can also be configured as follows.

The plant biosensor 1 needs to include the solar radiation sensor 10, the sap flow sensor 20, and the absorbed nutrient sensor 30. A part or all of the first casing 2, the communication device 11, the carbon dioxide sensor 14, the temperature and humidity sensor 15, and the VOC sensor 16 may be omitted.

The sap flow sensor 20 is not limited to the configuration including the second casing 21, the heater unit 22, the temperature sensor unit 23, and the flow rate measurement unit 27, and may adopt another configuration capable of measuring the flow rate of sap flowing through the body of a plant. For example, in plan view including the first direction and the second direction (see FIG. 4 and FIG. 5), the heater unit 22 and the temperature sensor unit 23 may be disposed so as to be positioned on the same side with respect to the main stem 101. This configuration makes it possible to simplify the structure of the sap flow sensor 20. The temperature sensor unit 23 may also be configured to serve as the flow rate measurement unit 27. The heater unit 22 is not limited to have a substantially V shape, and may have another shape (e.g., a substantially C shape formed by three or more surfaces) that can come into contact with the main stem 101. The heat transfer sheet 221 may be omitted. The pair of first elastic members 216 and 217 may be omitted. The position adjustment mechanism 24 may include an elastic member such as a coil spring instead of the position adjustment member 241. In this case, the elastic member may be disposed so as to bias the main body unit 231 of the temperature sensor unit 23 toward the main stem 101.

The absorbed nutrient sensor 30 is not limited to the configuration including the third casing 31, the holding part 32, and the nutritional state sensor unit 33, and may adopt another configuration capable of measuring the nutritional state of the plant. For example, the light-projecting unit 331 and the light-receiving unit 332 may be disposed to oppose each other with respect to the petiole 102. The holding part 32 needs to be configured to be capable of holding the petiole 102, and, instead of the biasing member 323, a configuration capable of retaining the holding state of the petiole 102 by the first holding member 321 and the second holding member 322 may be adopted. The recess 324 may be omitted. The pair of second elastic members 318 and 319 may be omitted.

The second casing 21 and the third casing 31 may be casings having the same shape. The sap flow sensor 20 and the absorbed nutrient sensor 30 may be integrally provided, and the second casing 21 may also be configured to serve as the third casing 31 (or the third casing 31 also serves as the second casing 21).

A place other than one end (e.g., the upper end of FIG. 1) of the first casing 2 may be provided with a display unit that displays a remaining battery level, a communication state, and the like, or a power switch.

The first measurement unit may be provided separately from the flow rate measurement unit 27. The arithmetic device 17 may also serve as the first measurement unit and the second measurement unit, or the first measurement unit, the second measurement unit, and the calculation unit may be provided in an external device (e.g., a server).

Various embodiments of the present disclosure have been described above in detail with reference to the drawings, and finally, various aspects of the present disclosure will be described. In the following description, as an example, reference numerals are also added.

According to a first aspect of the present disclosure, there is provided a plant biosensor 1 that measures environmental information and biological information of a plant, the plant biosensor 1 including:
    a solar radiation sensor 10 that measures a solar radiation amount with which the plant is irradiated;
    a sap flow sensor 20 that measures a flow rate of sap flowing in a body of the plant; and
    an absorbed nutrient sensor 30 that measures a nutritional state of the plant.

The plant biosensor 1 of a second aspect of the present disclosure further includes:
    a communication device 11 that transmits information regarding the solar radiation amount measured by the solar radiation sensor 10, a flow rate of the sap measured by the sap flow sensor 20, and a nutritional state of the plant measured by the absorbed nutrient sensor 30; and
    a first casing 2 that accommodates the solar radiation sensor 10 and the communication device 11 inside of first casing, wherein
    the first casing 2 includes
    a first connection part 12 to which the sap flow sensor 20 is connected, and
    a second connection part 13 to which the absorbed nutrient sensor 30 is connected,
    the solar radiation sensor 10 and the communication device 11 are disposed at one end of the first casing 2, and
    the first connection part 12 and the second connection part 13 are disposed at an other end of the first casing 2 opposing the one end.

The plant biosensor 1 of a third aspect of the present disclosure further includes
    a carbon dioxide sensor 14 that measures a carbon dioxide amount in air around the plant, wherein
    the carbon dioxide sensor 14 is accommodated in the first casing 2 and disposed in a middle of the one end and the other end of the first casing 2.

The plant biosensor 1 of a fourth aspect of the present disclosure further includes
    a temperature and humidity sensor 15 that measures temperature and humidity around the plant, wherein
    the temperature and humidity sensor 15 is accommodated in the first casing 2 and disposed in a middle of the one end and the other end of the first casing 2.

The plant biosensor 1 of a fifth aspect of the present disclosure further includes
    a VOC sensor 16 that measures a volatile organic compound amount in air around the plant, wherein
    the VOC sensor 16 is accommodated in the first casing 2 and disposed in a middle of the one end and the other end of the first casing 2.

In the plant biosensor 1 of a sixth aspect of the present disclosure,
    the plant includes a first structure part 101 through which sap flows, and
    the sap flow sensor 20 includes
    a second casing 21 that internally includes an accommodation part 25 provided with a heat insulation layer 26 on a surface, the second casing being attachable around a direction in which the first structure part 101 extends with respect to the first structure part 101,
    a heater unit 22 that is disposed inside the accommodation part 25 and heats the first structure part 101,
    a temperature sensor unit 23 that is disposed inside the accommodation part 25 and measures a temperature of sap flowing through the first structure part 101 on both sides with respect to the heater unit 22 in a first direction where the first structure part 101 extends in a state where the second casing 21 is attached to the first structure part 101, and
    a flow rate measurement unit 27 that measures a flow rate of sap flowing through the first structure part 101 based on a temperature of sap flowing through the first structure part 101 measured by the temperature sensor unit 23.

In the plant biosensor 1 of a seventh aspect of the present disclosure, the heater unit 22 and the temperature sensor unit 23 are disposed to face each other across the first structure part 101 in a second direction intersecting the second casing 21 in the first direction.

In the plant biosensor 1 of an eighth aspect of the present disclosure, the heater unit 22 and the temperature sensor unit 23 are disposed to be positioned on a same side with respect to the first structure part 101 in plan view including the first direction and a second direction intersecting the first direction.

In the plant biosensor 1 of a ninth aspect of the present disclosure, the second casing 21 includes a screw hole 218 that is disposed on a straight line L passing through the heater unit 22 and the temperature sensor unit 23, penetrates the second casing 21 in a direction where the straight line L extends, and is provided with a screw groove on an inner periphery, and the sap flow sensor 20 includes a position adjustment member 241 that extends from an outside of the accommodation part 25 to the inside of the accommodation part 25 via the screw hole 218, is connected to the temperature sensor unit 23, is provided with a screw thread fitted into the screw groove on an outer periphery, and is movable in a direction where the straight line L extends by being rotated about the straight line L.

In the plant biosensor 1 of a tenth aspect of the present disclosure, the heater unit 22 includes a first surface, and a second surface disposed to intersect the first surface, and each of the first surface and the second surface is provided with a heat transfer sheet 221 including elasticity, and each of the first surface and the second surface comes into contact with the first structure part 101 via the heat transfer sheet 221.

In the plant biosensor 1 of an eleventh aspect of the present disclosure, the second casing includes a pair of first through holes 214 and 215 that are provided at both respective ends in the first direction, penetrate the second casing 21 in the first direction, and are capable of disposing the first structure part 101, and a pair of first elastic members 216 and 217 that are provided in at least any of the pair of first through holes 214 and 215 and capable of holding the first structure part 101 in a second direction intersecting the first direction.

In the plant biosensor 1 of a twelfth aspect of the present disclosure, the plant includes a second structure part 102 through which sap flows, and the absorbed nutrient sensor 30 includes a third casing 31 that is attachable around a direction in which the second structure part 102 extends with respect to the second structure part 102, a holding part 32 that is provided inside the third casing 31 and capable of holding the second structure part 102 in a direction intersecting a direction in which the second structure part 102 extends, and a nutritional state sensor unit 33 that is provided inside the third casing 31 and capable of measuring a nutritional state of the second structure part 102.

In the plant biosensor 1 of a thirteenth aspect of the present disclosure, the holding part 32 includes a first holding member 321 that is disposed to be movable along a fourth direction intersecting a third direction in which the second structure part 102 extends in a state where the third casing 31 is attached to the second structure part 102, a second holding member 322 that is disposed to cause the third casing 31 to oppose the first holding member 321 in the fourth direction, and is fixed to the third casing 31, and a biasing member 323 that biases the first holding member 321 in the fourth direction and in a direction approaching the second holding member 322.

In the plant biosensor 1 of a fourteenth aspect of the present disclosure, each of the first holding member 321 and the second holding member 322 includes a recess 324 that is recessed in a direction away from each other and in which the second structure part 102 is disposed.

In the plant biosensor 1 of a fifteenth aspect of the present disclosure, the absorbed nutrient sensor 30 includes a light-projecting unit 331 that irradiates, with light, the second structure part 102 in a state of being attached with the third casing 31, and a light-receiving unit 332 that receives light from the second structure part 102.

In the plant biosensor 1 of a sixteenth aspect of the present disclosure, the light-projecting unit 331 includes a light-emitting element that generates light, and a light-projecting fiber that guides light generated by the light-emitting element to the second structure part 102, and the light-receiving unit 332 includes a light-receiving element that receives light, and a light-receiving fiber that guides light from the second structure part 102 to the light-receiving element 332.

In the plant biosensor 1 of a seventeenth aspect of the present disclosure, the light-projecting unit 331 and the light-receiving unit 332 are disposed on a same side with respect to the second structure part 102 in a state where the third casing 31 is attached to the second structure part 102 in plan view including a third direction in which the second structure part 102 extends in a state where the third casing 31 is attached to the second structure part 102 and a fourth direction intersecting the third direction, and the light-projecting fiber and the light-receiving fiber are disposed to have a V shape.

In the plant biosensor 1 of a eighteenth aspect of the present disclosure, the light-projecting unit 331 and the light-receiving unit 332 are disposed to oppose each other with respect to the second structure part 102 in a state where the third casing 31 is attached to the second structure part 102.

In the plant biosensor 1 of a nineteenth aspect of the present disclosure,
the third casing 31 includes
a pair of second through holes 316 and 317 that are provided at both respective ends in a third direction where the second structure part 102 extends in a state where the third casing 31 is attached to the second structure part 102, penetrate the third casing 31, and are capable of disposing the second structure part 102, and
a pair of second elastic members 318 and 319 that are provided in at least any of the pair of second through holes 316 and 317 and capable of holding the second structure part 102 in a fourth direction intersecting the third direction.

In the plant biosensor 1 of a twentieth aspect of the present disclosure,
a first measurement unit 27 that measures a photosynthesis amount performed in the plant from a flow rate of sap measured by the sap flow sensor 20;
a second measurement unit 38 that measures a vegetative growth degree of the plant from a nutritional state of the plant measured by the absorbed nutrient sensor 30; and
a calculation unit 17 that calculates a reproductive growth degree of the plant based on the photosynthesis amount of the plant measured by the first measurement unit 27 and the vegetative growth degree of the plant measured by the second measurement unit 38.

By appropriately combining any embodiments or modifications among the various embodiments or modifications, it is possible to achieve respective effects they have. Combinations of embodiments, combinations of examples, or combinations of embodiments and examples are possible, and combinations of features in different embodiments or examples are also possible.

Although the present disclosure has been fully described in connection with preferred embodiments with reference to the accompanying drawings, various modifications and corrections will be obvious to those skilled in the art. Such modifications and corrections are to be understood as being included within the scope of the present disclosure as long as they do not depart from the appended claims.

INDUSTRIAL APPLICABILITY

The plant biosensor of the present disclosure can be applied to a plant cultivated in a greenhouse, for example.

DESCRIPTION OF REFERENCE CHARACTERS 1 plant biosensor
2 first casing
10 solar radiation sensor
11 communication device
12 first connection part
13 second connection part
14 carbon dioxide sensor
15 temperature and humidity sensor
16 VOC sensor
17 arithmetic device
20 sap flow sensor
21 second casing
211 member
212 opening surface
213 hinge
214, 215 through hole
216, 217 elastic member
218 screw hole
219 boss part
22 heater unit
221 heat transfer sheet
23 temperature sensor unit
231 main body unit
232 temperature sensor
24 position adjustment mechanism
241 position adjustment member
242 operation unit
25 accommodation part
26 heat insulation layer
27 flow rate measurement unit
29 connection mechanism
30 absorbed nutrient sensor
31 third casing
311 first member
312 second member
313 hinge
314 member
315 opening surface
316, 317 through hole
318, 319 elastic member
32 holding part
321 first holding member
322 second holding member
323 biasing member
324 recess
33 nutritional state sensor unit
331 light-projecting unit
332 light-receiving unit
34 connection part
35 cable attachment part
36 connection mechanism
37 band attachment part
38 growth degree measurement unit
41 electrical cable
42 optical fiber
101 main stem
102 petiole
110 banding band
120 cable
200, 300 image
210 first display region
220 second display region
310, 320 region
L straight line

The invention claimed is:
1. A plant biosensor that measures environmental information and biological information of a plant, the plant biosensor comprising:
a solar radiation sensor that measures a solar radiation amount with which the plant is irradiated;
a sap flow sensor that measures a flow rate of sap flowing in a body of the plant; and
an absorbed nutrient sensor that measures a nutritional state of the plant, wherein
the plant includes a first structure part through which sap flows,
the sap flow sensor includes
a second casing that internally includes an accommodation part provided with a heat insulation layer on a surface, the second casing being attachable around a direction in which the first structure part extends with respect to the first structure part,
a heater unit that is disposed inside the accommodation part and heats the first structure part, a temperature sensor unit that is disposed inside the accommodation part and measures a temperature of sap flowing through the first structure part on both sides with respect to the heater unit in a first direction where the first structure part extends in a state where the second casing is attached to the first structure part, and a flow rate measurement unit that measures a flow rate of sap flowing through the first structure part based on a temperature of sap flowing through the first structure part measured by the temperature sensor unit, the heater unit and the temperature sensor unit are disposed to be positioned on a same side with respect to the first structure part in plan view including the first direction and a second direction intersecting the first direction, the second casing includes
a screw hole that is disposed on a straight line passing through the heater unit and the temperature sensor unit, penetrates the second casing in a direction where the straight line extends, and is provided with a screw groove on an inner periphery, and the sap flow sensor includes
a position adjustment member that extends from an outside of the accommodation part to the inside of the accommodation part via the screw hole, is connected to the temperature sensor unit, is provided with a screw thread fitted into the screw groove on an outer periphery, and is movable in a direction where the straight line extends by being rotated about the straight line.

2. The plant biosensor according to claim 1 further comprising:
a communication device that transmits information regarding the solar radiation amount measured by the solar radiation sensor, a flow rate of the sap measured by the sap flow sensor, and a nutritional state of the plant measured by the absorbed nutrient sensor; and
a first casing that accommodates the solar radiation sensor and the communication device inside of first casing, wherein
the first casing includes
a first connection part to which the sap flow sensor is connected, and
a second connection part to which the absorbed nutrient sensor is connected,
the solar radiation sensor and the communication device are disposed at one end of the first casing, and
the first connection part and the second connection part are disposed at an other end of the first casing opposing the one end.

3. The plant biosensor according to claim 2 further comprising
a carbon dioxide sensor that measures a carbon dioxide amount in air around the plant, wherein
the carbon dioxide sensor is accommodated in the first casing and disposed in a middle of the one end and the other end of the first casing.

4. The plant biosensor according to claim 2 further comprising
a temperature and humidity sensor that measures temperature and humidity around the plant, wherein
the temperature and humidity sensor is accommodated in the first casing and disposed in a middle of the one end and the other end of the first casing.

5. The plant biosensor according to claim 2 further comprising
a VOC sensor that measures a volatile organic compound amount in air around the plant, wherein
the VOC sensor is accommodated in the first casing and disposed in a middle of the one end and the other end of the first casing.

6. The plant biosensor according to claim 1, wherein
the heater unit includes
a first surface, and
a second surface disposed to intersect the first surface, and
each of the first surface and the second surface is provided with a heat transfer sheet including elasticity, and each of the first surface and the second surface comes into contact with the first structure part via the heat transfer sheet.

7. The plant biosensor according to claim 1, wherein
the second casing includes
a pair of first through holes, each of the pair of first through holes being provided at both respective ends in the first direction, penetrating the second casing in the first direction, and being capable of disposing the first structure part, and
a pair of first elastic members that are provided in at least any of the pair of first through holes and capable of holding the first structure part in a second direction intersecting the first direction.

8. The plant biosensor according to claim 1, wherein
the plant includes a second structure part through which sap flows, and
the absorbed nutrient sensor includes
a third casing that is attachable around a direction in which the second structure part extends with respect to the second structure part,
a holding part that is provided inside the third casing and capable of holding the second structure part in a direction intersecting a direction in which the second structure part extends, and
a nutritional state sensor unit that is provided inside the third casing and capable of measuring a nutritional state of the second structure part.

9. The plant biosensor according to claim 8, wherein
the holding part includes
a first holding member that is disposed to be movable along a fourth direction intersecting a third direction in which the second structure part extends in a state where the third casing is attached to the second structure part,
a second holding member that is disposed to oppose the first holding member in the fourth direction, and is fixed to the third casing, and
a biasing member that biases the first holding member in the fourth direction and in a direction approaching the second holding member.

10. The plant biosensor according to claim 9, wherein
each of the first holding member and the second holding member includes a recess that is recessed in a direction away from each other and in which the second structure part is disposed.

11. The plant biosensor according to claim 8, wherein
the absorbed nutrient sensor includes
a light-projecting unit that irradiates, with light, the second structure part in a state of being attached with the third casing, and
a light-receiving unit that receives light from the second structure part.

12. The plant biosensor according to claim 11, wherein the light-projecting unit includes
a light-emitting element that generates light, and
a light-projecting fiber that guides light generated by the light-emitting element to the second structure part, and
the light-receiving unit includes
a light-receiving element that receives light, and
a light-receiving fiber that guides light from the second structure part to the light-receiving element.

13. The plant biosensor according to claim 12, wherein the light-projecting unit and the light-receiving unit are disposed on a same side with respect to the second structure part in a state where the third casing is attached to the second structure part in plan view including a third direction in which the second structure part extends in a state where the third casing is attached to the second structure part and a fourth direction intersecting the third direction, and
the light-projecting fiber and the light-receiving fiber are disposed to have a V shape.

14. The plant biosensor according to claim 12, wherein the light-projecting unit and the light-receiving unit are disposed to oppose each other with respect to the second structure part in a state where the third casing is attached to the second structure part.

15. The plant biosensor according to claim 8, wherein the third casing includes
a pair of second through holes, each of the pair of second through holes being provided at both respective ends in a third direction where the second structure part extends in a state where the third casing is attached to the second structure part, penetrating the third casing, and being capable of disposing the second structure part, and
a pair of second elastic members that are provided in at least any of the pair of second through holes and capable of holding the second structure part in a fourth direction intersecting the third direction.

16. A sap flow sensor that measures a flow rate of sap flowing in a body of a plant including a first structure part through which sap flows, the sap flow sensor comprising:
a second casing that internally includes an accommodation part provided with a heat insulation layer on a surface, the second casing being attachable around a direction in which the first structure part extends with respect to the first structure part;
a heater unit that is disposed inside the accommodation part and heats the first structure part;
a temperature sensor unit that is disposed inside the accommodation part and measures a temperature of sap flowing through the first structure part on both sides with respect to the heater unit in a first direction where the first structure part extends in a state where the second casing is attached to the first structure part; and
a flow rate measurement unit that measures a flow rate of sap flowing through the first structure part based on a temperature of sap flowing through the first structure part measured by the temperature sensor unit, wherein
the heater unit and the temperature sensor unit are disposed to face each other across the first structure part in a second direction intersecting the second casing in the first direction, and
the second casing includes
a screw hole that is disposed on a straight line passing through the heater unit and the temperature sensor unit, penetrates the second casing in a direction where the straight line extends, and is provided with a screw groove on an inner periphery, and
a position adjustment member that extends from an outside of the accommodation part to the inside of the accommodation part via the screw hole, is connected to the temperature sensor unit, is provided with a screw thread fitted into the screw groove on an outer periphery and is movable in a direction where the straight line extends by being rotated about the straight line.

17. The sap flow sensor according to claim 16, wherein the second casing includes
a pair of first through holes, each of the pair of first through holes being provided at both respective ends in the first direction, penetrating the second casing in the first direction, and being capable of disposing the first structure part, and
a pair of first elastic members that are provided in at least any of the pair of first through holes and capable of holding the first structure part in a second direction intersecting the first direction.

18. A sap flow sensor that measures a flow rate of sap flowing in a body of a plant including a first structure part through which sap flows, the sap flow sensor comprising:
a second casing that internally includes an accommodation part provided with a heat insulation layer on a surface, the second casing being attachable around a direction in which the first structure part extends with respect to the first structure part;
a heater unit that is disposed inside the accommodation part and heats the first structure part;
a temperature sensor unit that is disposed inside the accommodation part and measures a temperature of sap flowing through the first structure part on both sides with respect to the heater unit in a first direction where the first structure part extends in a state where the second casing is attached to the first structure part; and
a flow rate measurement unit that measures a flow rate of sap flowing through the first structure part based on a temperature of sap flowing through the first structure part measured by the temperature sensor unit, wherein
the heater unit includes
a first surface, and
a second surface disposed to intersect the first surface, and
each of the first surface and the second surface is provided with a heat transfer sheet including elasticity, and each of the first surface and the second surface comes into contact with the first structure part via the heat transfer sheet.

19. The sap flow sensor according to claim 18, wherein the second casing includes
a pair of first through holes, each of the pair of first through holes being provided at both respective ends in the first direction, penetrating the second casing in the first direction, and being capable of disposing the first structure part, and
a pair of first elastic members that are provided in at least any of the pair of first through holes and capable of holding the first structure part in a second direction intersecting the first direction.

* * * * *